United States Patent [19]

Schick

[11] Patent Number: 5,472,598
[45] Date of Patent: Dec. 5, 1995

[54] CONNECTION ASSEMBLY FOR LIQUID CHROMATOGRAPHY COLUMNS

[75] Inventor: Hans G. Schick, Anacortes, Wash.

[73] Assignee: Upchurch Scientific, Inc., Oak Harbor, Wash.

[21] Appl. No.: 227,976

[22] Filed: Apr. 15, 1994

[51] Int. Cl.$^6$ .................................................. B01D 15/08
[52] U.S. Cl. ..................................... 210/198.2; 210/656
[58] Field of Search .................................... 210/635, 656, 210/198.2, 232, 238, 541; 96/101, 104, 106

[56] References Cited

U.S. PATENT DOCUMENTS

| | | | |
|---|---|---|---|
| 3,583,230 | 6/1971 | Patterson | 210/198.2 |
| 3,682,315 | 8/1972 | Haller | 210/198.2 |
| 3,763,879 | 10/1973 | Jaworek | 210/198.2 |
| 3,855,130 | 12/1974 | Randau | 210/198.2 |
| 3,878,099 | 4/1975 | Ogle | 210/198.2 |
| 3,904,527 | 9/1975 | Wilhelmson | 210/198.2 |
| 3,926,800 | 12/1975 | Stephens | 210/198.2 |
| 4,093,550 | 6/1978 | Stahl | 210/198.2 |
| 4,187,177 | 2/1980 | Stahl | 210/198.2 |
| 4,283,280 | 8/1981 | Brownlee | 210/198.2 |
| 4,293,415 | 10/1981 | Bente | 210/198.2 |
| 4,313,828 | 2/1982 | Brownlee | 210/198.2 |
| 4,389,313 | 6/1983 | Charney | 210/198.2 |
| 4,451,364 | 5/1984 | Higgins | 210/198.2 |
| 4,522,715 | 6/1985 | Walters | 210/198.2 |
| 4,563,275 | 1/1986 | McEachern | 210/198.2 |
| 4,565,631 | 1/1986 | Hatch | 210/198.2 |
| 4,565,632 | 6/1986 | Hatch et al. | 210/656 |
| 4,587,014 | 5/1986 | America | 210/198.2 |
| 4,737,284 | 4/1988 | Haucke | 210/198.2 |
| 4,755,293 | 7/1988 | Sakamoto | 210/198.2 |
| 4,758,340 | 7/1988 | Marchand | 210/450 |
| 4,769,141 | 9/1988 | Couillard | 210/199.2 |
| 4,784,772 | 11/1988 | Gotoh | 210/638 |
| 4,861,473 | 8/1989 | Shackelford | 210/198.2 |
| 4,876,005 | 10/1989 | America | 210/198.2 |
| 4,968,421 | 11/1990 | Spacek | 210/198.2 |
| 5,131,818 | 7/1992 | Wittkop | 417/273 |
| 5,169,522 | 12/1992 | Shalon | 210/198.2 |
| 5,194,225 | 5/1993 | Muller | 210/198.2 |
| 5,238,556 | 8/1993 | Shirkhan | 210/656 |

OTHER PUBLICATIONS

Upchurch Scientific, Inc., "Catalog of Chromatography and Fluid Transfer Fittings" (1993), pp. 84–91.
Upchurch Scientific, Inc. "Chromatography Fittings and Accessories Catalog and Technical Reference Manual" (1992), pp. 84–91.
Supelco, Inc. "Tech Novations" magazine (Jul./Aug. 1993), pp. 18–19.
ES Industries "HPLC Columns, Packings and Accessories" catalog (Jan. 1990), pp. 36–37.
Phase Separations, Inc., "Spherisorb" catalog, part number 971014 (undated) pp. 1 fold–out page and 10–11.
Keystone Scientific, Inc., "HPLC & SFC Catalog" (1992–93), pp. 5, 21, 23, 27, 33, 34, 37, 43, 56, 78, 79, 81, 83 and 85.
Vydac, "HPLC Columns and Separation Materials" catalog (1992), p. 29.

(List continued on next page.)

*Primary Examiner*—Ernest G. Therkorn
*Attorney, Agent, or Firm*—Vinson & Elkins

[57] ABSTRACT

An assembly allowing the quick and easy connection or replacement of a column in a LC system. The assembly includes a cooperating male twist lock member and a female twist lock member. When rotated relative to one another, the male member and female member are removably attached. When attached, the assembly provides a leak-free seal at one end of a guard column, with the other end of the guard column attached to a LC system through tubing which is secured to a holder in which the guard column is positioned. In the preferred embodiment of the invention, the assembly is biocompatible and presents only chemically inert surfaces to the flow of the mobile phase and sample.

16 Claims, 5 Drawing Sheets

OTHER PUBLICATIONS

Alltech Associates, Inc., "Ion Chromatography Accessories and Instrumentation" bulletin #217 (1992), p. 36.

Bodman, "HPLC Pocket Guide" (1991), p. 34.

Supelco, Inc., "Tech Novations" magazine (Mar./Apr. 1993), p. 29.

Supelco, Inc., "Tech Novations" magazine, issue 1 (1992), p. 5.

Alltech Associates, Inc., "Chromatography" catalog 300 (1993), pp. 428, 514–515.

Alltech Associates, Inc., "Chromatography" catalog 250 (1991), pp. 566–567, 419, 478–479, 395–399.

Baxter Diagnostics, Inc., "Chromatography Catalog" (1992), pp. 261–262, 499–500.

Chrom Tech, Inc., "Chromatography Supplies and Accessories" catalog (1992), pp. 88, 90, 147, 171–172, 229.

Keystone Scientific, Inc., "HPLC & SFC Catalog" (1992–1993), p. 66.

Whatman, Inc., "Chromatography Product Guide" (1991), pp. 3, 6.

Alltech Associates, Inc., "Filters" bulletin #190 A (1991), p. 9.

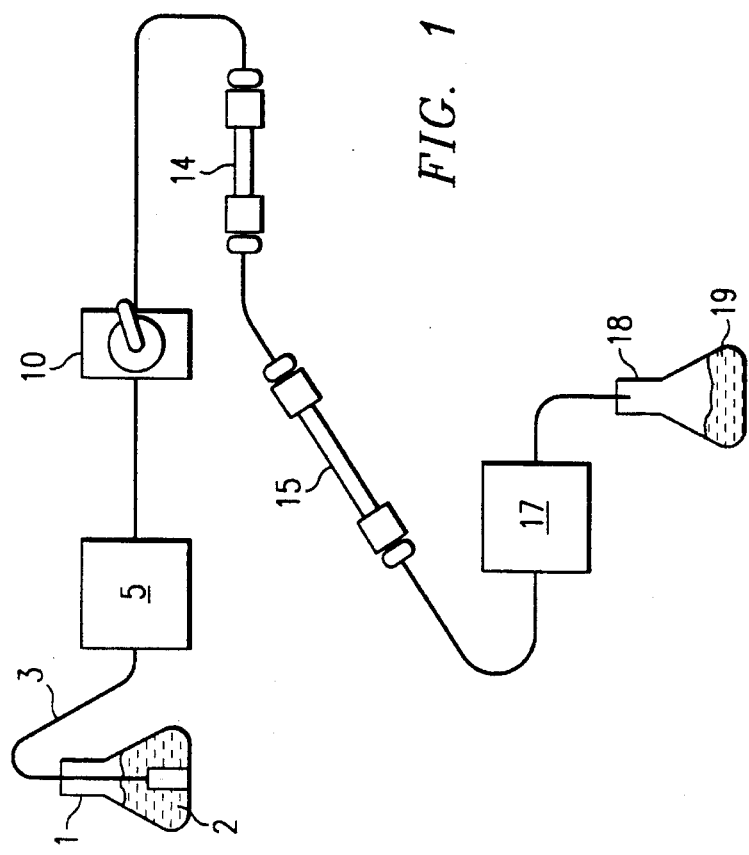
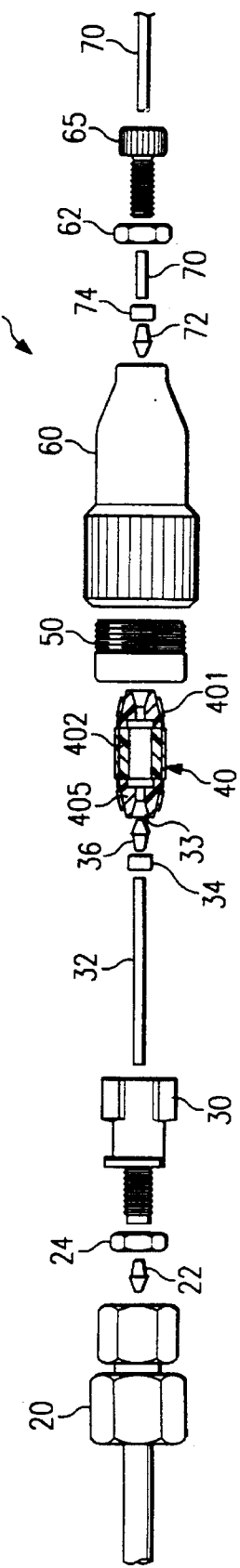
FIG. 1
FIG. 2

CONNECTION ASSEMBLY FOR LIQUID CHROMATOGRAPHY COLUMNS

FIELD OF THE INVENTION

This invention relates generally to an assembly for use in connecting components of liquid chromatography systems, and relates more particularly to an assembly well-suited for allowing quick connections and disconnections of liquid chromatography columns.

BACKGROUND OF THE INVENTION

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components. A more detailed description of the separation process can be found, among other places, in Chapters 2 and 5 of *Introduction to Modem Liquid Chromatography* (2d ed. 1979) by L. R. Snyder and J. J. Kirkland, which chapters are incorporated by reference herein.

Once the sample (with its components now separated) leaves the column, it flows with the mobile phase past a detector. The detector detects the presence of specific molecules or compounds. As discussed in Chapter 4 of *Introduction to Modem Liquid Chromatography*, which chapter is incorporated by reference herein, two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

It will be understood to those skilled in the art that, as used herein, the term "LC system" is intended in its broad sense to include all apparatus used in connection with liquid chromatography, whether made of only a few simple components or made of numerous, sophisticated components which are computer controlled or the like.

Many different types of LC systems and components for LC systems are commercially available from a number of vendors. For example, Millipore Corporation of Milford, Mass., Beckman Instruments of Fullerton, Calif., and Hewlett-Packard Co. of Palo Alto, Calif., all sell LC systems, including pumps, sample injection valves, columns, and detectors, among other things. In addition, various columns with various packings are commercially available from a variety of sources, including (among others) Upchurch Scientific, Inc., of Oak Harbor, Wash., and Baxter Healthcare Corporation of Deerfield, Ill.

Today, most LC systems include pumps which can generate relatively high pressures of up to around 6,000 psi. In many situations, an operator can obtain successful results by operating a LC system at "low" pressures of anywhere from just a few psi or so up to 1,000 psi or so. More often than not, however, an operator will find it desirable to operate a LC system at relatively "higher" pressures of over 1,000 psi. The operation and use of LC systems at such "higher" pressure levels is often referred to as "high pressure liquid chromatography" or "high performance liquid chromatography" (HPLC).

In practice, various components may be connected by an operator to perform a given task. For example, an operator will select an appropriate mobile phase and column, then connect a supply of the selected mobile phase and a selected column to the LC system before operation. In order to be suitable for HPLC applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's ions remain in the tubing and do not pass the detector. Perhaps of even greater concern, however, is the fact that ions from the stainless steel tubing may detach from the tubing and flow past the detector, thus leading to potentially erroneous results. Hence, there is a need for "biocompatible" connections through the use of a material which is chemically inert with respect to such "biological" samples and the mobile phase used with such samples so that ions will not be released by the tubing and thus contaminate the sample.

Therefore, it is an object of the present invention to provide a mechanism allowing an operator to quickly disconnect or connect a column to a LC system.

It is another object of the present invention to provide a mechanism to reduce inefficiency and wasted time in connecting or disconnecting a column in a LC system.

It is yet another object of the present invention to provide a mechanism to allow an operator to quickly replace a column in a LC system.

It is yet another object of the present invention to provide a mechanism to allow an operator to quickly and easily achieve a leak-free connection of a column to a LC system.

It is still another object of the present invention to provide a biocompatible assembly to allow an operator to quickly and easily achieve a biocompatible connection of a column in a LC system.

The above and other advantages of the present invention will become readily apparent to those skilled in the art from the following detailed description of the present invention, and from the attached drawings, which are briefly described below.

SUMMARY OF THE INVENTION

The present invention may be implemented by the use of a male twist lock member and a female twist lock member which are adapted to engage and hold each other. In one embodiment, one end of a primary column is attached to the male twist lock member, through which tubing extends. A replaceable guard column is placed on the extended tubing. A female twist lock member, securely attached to and within a holder, is placed over the guard column and one end of the male twist lock member. The male and female members have portions adapted to engage and hold the other. A pair of shoulders on the male member are inserted past cooperating shoulders in the female member. The two members are rotated relative to one another to thereby engage and hold one another. Because the shoulders are adapted to be inclined, the rotation also forces the extending tubing into the first port of the guard column and creates a leak-free seal. The female member is attached to a holder which is adapted to hold the guard column. At the other end of the holder, opposite the female twist lock member, a threaded counterbore is provided to allow the connection of the guard column to a LC system through the second port of the guard column.

In its preferred embodiment, the quick release mechanism is made with biocompatible materials.

BRIEF DESCRIPTION OF THE DRAWINGS

FIG. 1 is a block diagram of a conventional LC system.

FIG. 2 is an exploded view of various components of the quick release mechanism of the present invention.

DETAILED DESCRIPTION OF THE INVENTION

Figure 3:
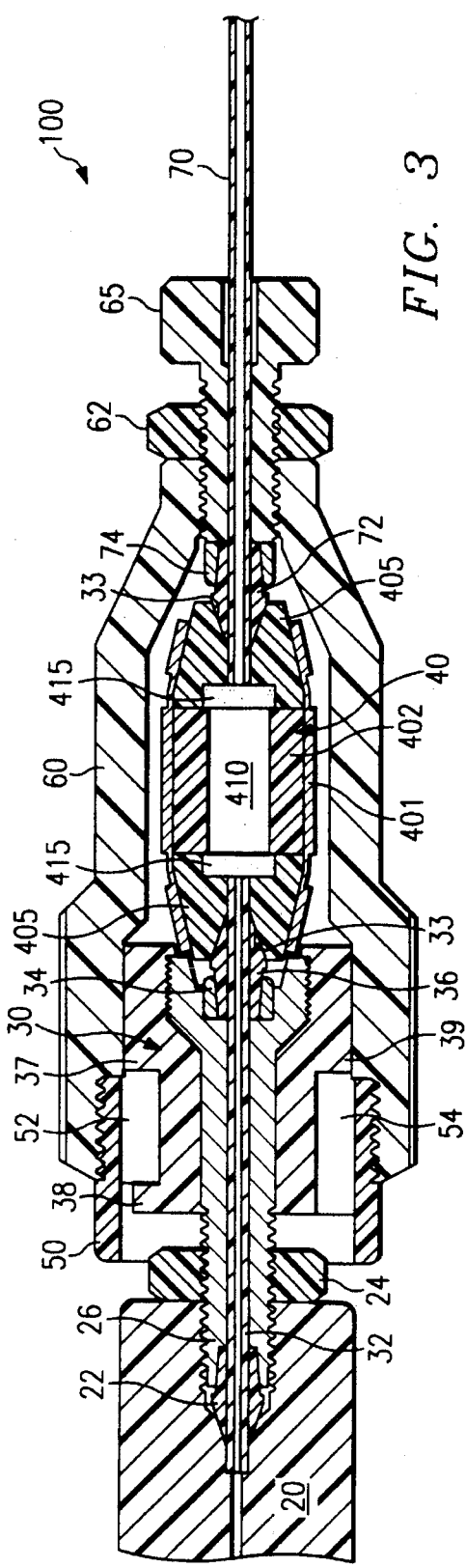
FIG. 3 is a cross-sectional view of the quick release mechanism of the present invention, showing a guard column connected to a LC system.

In FIG. 1, a block diagram of the essential elements of a conventional LC system is provided. A reservoir 1 contains a solvent or mobile phase 2. Tubing 3 connects the mobile phase 2 in the reservoir 1 to a pump 5. The pump 5 is connected to a sample injection valve 10 which, in turn, is connected via tubing to a first end of a guard column 14. The second end of the guard column 14 is in turn connected to the first end of a primary column 15. The second end of the primary column 15 is then connected via tubing to a detector 17. After passing through the detector 17, the mobile phase 2 and the sample injected via injection valve 10 are expended into a second reservoir 18, which contains the chemical waste 19. As noted above, the sample injection valve 10 is used to inject a sample of a material to be studied into the LC system. The mobile phase 2 flows through the tubing 3 which is used to connect the various elements of the LC system together.

When the sample is injected via sample injection valve 10 in the LC system, the sample is carried by the mobile phase through the tubing into the column 15. As is well known in the art, the column 15 contains a packing material which acts to separate the constituent elements of the sample. After exiting the column 15, the sample (as separated via the column 15) then is carried to and enters a detector 17, which detects the presence or absence of various chemicals. The information obtained by the detector 17 can then be stored and used by an operator of the LC system to determine the constituent elements of the sample injected into the LC system.

Referring now to FIG. 2, a guard column 40 can be attached to a conventional primary column 20 (which can be an analytical column or a preparative column) by means of a novel connection mechanism 100. The connection mechanism 100 includes a tube 32, a ferrule 22, a lock nut 24, a male twist lock member 30, a guard column 40, another ferrule 36, a ring 34, a female twist lock 50, a holder 60, and another ferrule 72 and ring 74 for connecting tubing 70 to the holder 60 by using a lock nut 62 and an adjustment nut 65. The following discussion addresses the preferred embodiment of the present invention.

The guard column 40 is shown in FIGS. 2 and 3 in a cross sectional view, revealing the use of an outer, metal tube 401 within which an inner tube 402 is positioned. At each end of the guard column 40 is an end fitting 33. A more detailed description of the preferred embodiment of the guard column 40 can be found in my co-pending application for U.S. Letters Patent titled "Column for Liquid Chromatography," filed Apr. 15, 1994, which is incorporated by reference herein.

Referring now to FIG. 3, a cross-sectional view of the mechanism as assembled and connected to a LC system is provided. In FIG. 3, one end of a male adapter 26 is screwed into a threaded counterbore of the column 20. Although this discussion addresses the counterbore of the column 20, the following discussion will be understood by those skilled in the art to be equally applicable to situations involving a threaded counterbore of an end fitting of a primary column (not shown). A ferrule 22 is pressed against the column 20 by screwing the threaded portion of the adapter 26 into the threaded counterbore of the column 20, thus providing a leak-free seal between the hollow tubing 32 and the interior of the column 20. A lock nut 24 is screwed onto the threaded end of the adapter 26 to ensure that adapter 26 stays firmly secured to the column 20.

As shown in FIG. 3, the male twist lock member 30 is firmly secured to the adapter 26. For best results, I prefer to screw the adapter 26 into the male member 30 after dabbing glue on the threads, thus permanently and securely attaching adapter 26 and male member 30 to each other. Preferably, the adapter 26 and the male member 30 are attached to none another before they are attached to the other components in the connection assembly 100.

Still referring to FIG. 3, a female twist lock member 50 is positioned around the outside of the male twist lock member 30. The shoulders 52 and 54 of the female twist lock 50 are adapted and designed to engage and hold the shoulders 37 and 39 of the male twist lock member 30. As shown in FIG. 3, the shoulders 52 and 54 of the female lock member 50 hold the male lock member 30 in place and prevent the removal or separation of the male lock member 30 from the female lock member 50.

The male twist lock member 30 also has a lip 38. The lip 38 is designed and adapted so that, when the male member 30 and female member 50 are rotated more than 90° relative to each other, the lip 38 abuts one of the shoulders 52 and 54 of the female member 50, thus preventing the further rotation of the male member 30 and the female member 50 relative to each other. Hence, lip 38 provides a rotational stop by preventing the rotation of the male twist lock member 30 and the female member 50 more than about 90° relative to each other. Without lip 38, the shoulders 37 and 39 of the male member 30 and the shoulders 52 and 54 of the female member 50 would re-align when rotated 180° so as to allow the easy separation of the male member 30 and the female member 50.

Still referring to FIG. 3, a hollow holder 60 is shown with a first end attached to the female twist lock member 50. The female twist lock member 50 has been securely attached to the holder 60 by screwing the threaded portion of the female twist lock member 50 into the threaded counterbore at the first end of the holder 60. For best results, I prefer to use glue on the threads of the female member 50 to ensure a permanent attachment of female member 50 and the holder 60. As shown in FIG. 3, the holder 60 is hollow and is adapted to hold the male twist lock member 30, a guard column 40, and the appropriate components (described below) to connect the guard column 40 to the tubing 32 which extends from the adapter 26 and the male twist lock member 30, as well as to the tubing 70 which connects the guard column 40 to the LC system (not shown in FIG. 3).

Still referring to FIG. 3, the guard column 40 includes an outer, metal tube 401, an inner tube 402, and end fittings 405. The end fittings 405 have a conical-shaped port 33 to allow connection of the guard column 40 to other components in an LC system. In addition, frits 415 are located in the guard column 40. As can be seen from FIG. 3, the ferrules 36 and 72 are adapted to fit securely and snugly into the ports 33 of the guard column 40, thus ensuring a leak-free seal. It will be understood by those skilled in the art, however, that the ports 33 of the guard column 40 need not be conical. Instead, the ports 33 could be flat-bottomed and the ferrules 36 and 72 could be of an appropriate shape and size to securely attach tubing 32 and tubing 70 to the ports 33.

As can be seen from FIG. 3, there is no nut or the like to allow an operator to apply direct pressure to force the ring 34 and ferrule 36 against the conical port 33 of guard column 40 to obtain a leak-free connection of the tubing 32 and the interior of the guard column 40. Instead, an adjustment nut 65, together with a ring 74 and a ferrule 72, are used to force the guard column 40 against the tubing 32 and the ferrule 36. (A more detailed discussion of the operation of the connection assembly 100 is provided below.) As shown in FIG. 3, a piece of tubing 70 extends through the adjustment nut 65, the lock nut 62, and the ring 74 and ferrule 72. The adjustment nut 65 is screwed into a threaded counterbore at the second end of the holder 60, thus forcing the ferrule 72 and the tubing 70 against the second port 33 of the guard column 40. By selectively tightening the adjustment nut 65, enough pressure is applied so that, when the male member 30 and the female member 50 are joined and rotated (as described below), there is sufficient pressure to form leak-free connections at both ports 33 of the guard column 40. The lock nut 62 is provided to secure the adjustment nut 65 in place so that, once properly assembled, the adjustment nut 65 will not slip or move.

Those skilled in the an will appreciate that the sizes of the various components in the mechanism 100 will depend on one another. For example, the tubing 32 needs to extend from the bottom of the port in column 20 to the bottom of the port 33 in the guard column 40. If the tubing 32 is too long, it may not be possible to obtain a sealing connection which can withstand the operating pressure of HPLC applications. A solution to this problem is discussed below in connection with the operation of the assembly 100. Similarly, the shoulders 52 and 54 of the female member 50 are adapted to match the shoulders 37 and 39 of the male member 30.

Figure 5:
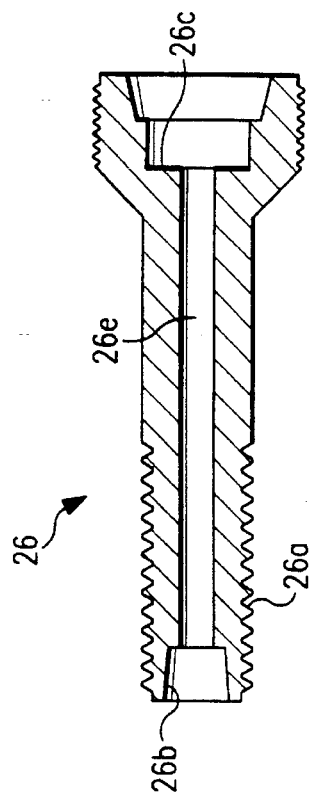
FIG. 5 is a cross-sectional view of a male adapter.
Figure 6:
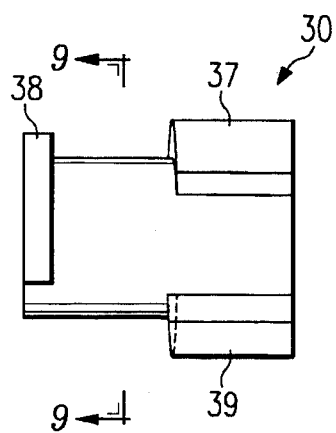
FIG. 6 is a side view of the male twist lock member.
Figure 7:
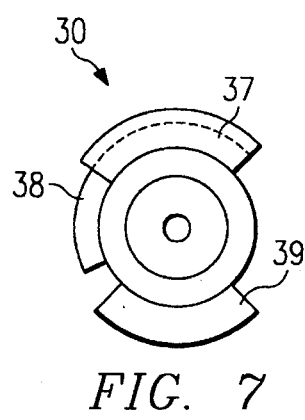
FIG. 7 is a top view of the male twist lock member.
Figure 9:
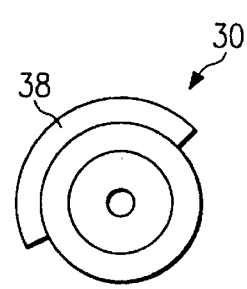
FIG. 9 is a cross-sectional view of the male twist lock member taken along line 9—9.

Referring now to FIGS. 4–9, the male twist lock member 30 is shown in greater detail. As shown best in FIGS. 4 and 6, a first end of the male member 30 has two shoulders 37 and 39. Shoulders 37 and 39 extend radially outward from the body of member 30. As shown in FIGS. 6 and 7, shoulders 37 and 39 are preferably different in size, so that one extends a greater arcuate distance around the central body of member 30 than the other. As shown in FIG. 7, shoulder 37 extends an arcuate distance of about 100°, while shoulder 39 extends for an arc of only about 90°. As best shown in FIGS. 6–9, the male member 30 also includes a lip 38 at the end opposite the end which has shoulders 37 and 39. Lip 38 also extends radially outward from the central body of male member 30. As indicated in FIG. 7, lip 38 extends a greater arcuate distance around the central body of the member 30 than either of shoulders 37 and 39. For best results, I prefer to have lip 38 extend for an arc of about 160° around the longitudinal axis of the male member 30. As shown in FIG. 6, the depth of lip 38 is also much less than that of either shoulder 37 or shoulder 39.

Figure 4:
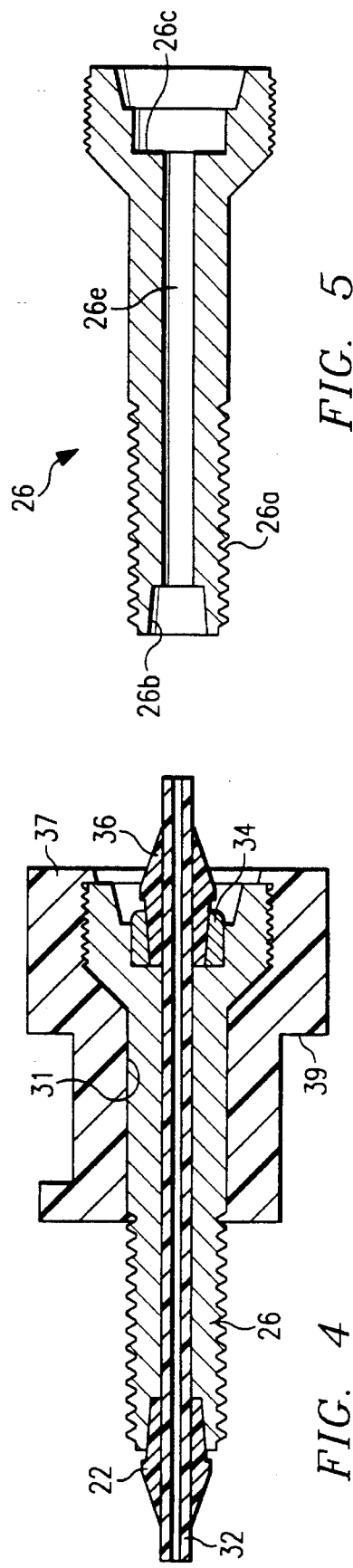
FIG. 4 is a cross-sectional view of the male twist lock member subassembly of the present invention.

Referring back to FIG. 4, the male member 30 has a hollow passageway 31 extending longitudinally through its body. Firmly secured within the passageway 31 is an adapter 26. FIG. 5 shows the adapter 26 by itself and before attachment to the male member 30. One portion 26a of the adapter 26 is threaded to allow the adapter 26 to be screwed into an end fitting of a column 20 (as shown in FIG. 3). The opposite end also has threads 26d for securely holding the adapter 26 in place within the body of the male twist lock member 30, as is shown in FIG. 4. As also shown in FIGS. 4 and 5, the adapter 26 has a hollow passageway 26e therethrough, which is adapted to hold a piece of tubing 32 therein (as shown in FIG. 4). Still referring to FIG. 5, the adapter 26 also has a seat 26b which is adapted to receive and hold a ferrule 22 (as shown in FIG. 4). The seat 26c is similarly adapted to receive and hold a ring 34 used in combination with the ferrule 36 (as shown in FIG. 4). For best results, I prefer to use an adapter 26 made of stainless steel, although aluminum or other metals could be used.

Figure 10:
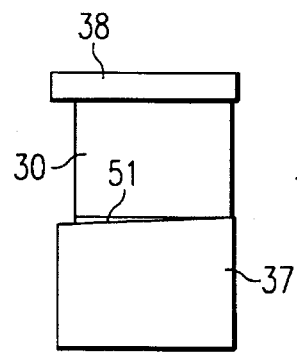
FIG. 10 is another side view of the male twist lock member.
Figure 8:
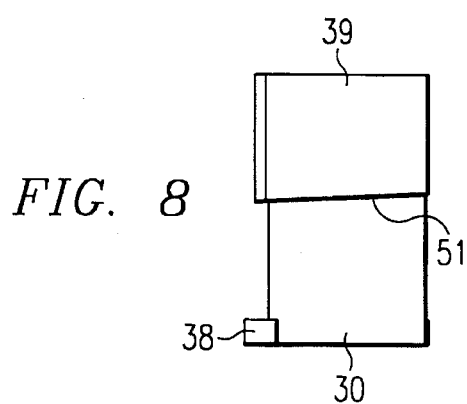
FIG. 8 is another, different side view of the male twist lock member.

As best shown in FIGS. 8 and 10, each of the shoulders 37 and 39 of the male member 30 have an inclined edge 51. As detailed below, the inclined edges 51 cooperate with corresponding inclined edges 53 of the shoulders 52 and 54 of the female twist lock member 50. For best results, I prefer to have an incline sufficient so that, when the male member 30 is inserted into the female member 50 and they are rotated 90° relative to one another, the inclined edges 51 and 53 require that the male member 30 and the guard column 40 travel about 0.016 inches further towards each other. This extra distance ensures that the connections to the ports 33 of the guard column 40 will be leak free.

Figure 15:
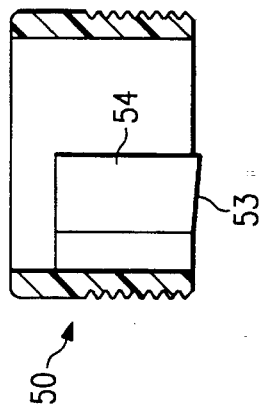
FIG. 15 is a cross-sectional view of the female twist lock member taken along line 14—14.
Figure 12:
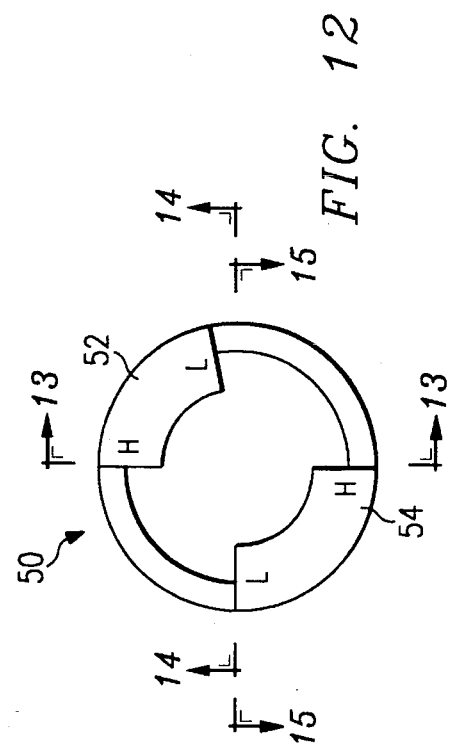
FIG. 12 is a bottom view of the female twist lock member.
Figure 14:
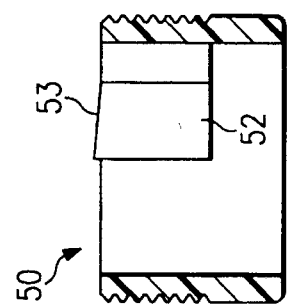
FIG. 14 is a cross-sectional view of the female twist lock member taken along line 14—14.
Figure 13:
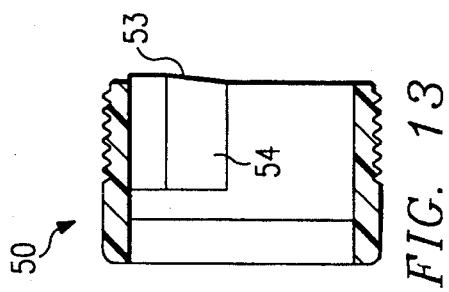
FIG. 13 is a cross-sectional view of the female twist lock member taken along line 13—13.
Figure 11:
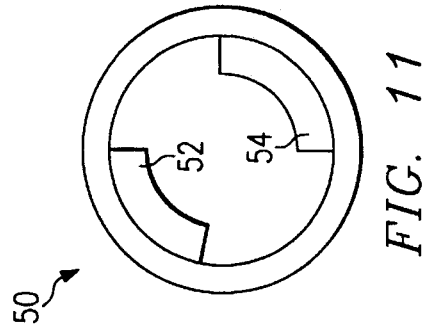
FIG. 11 is a top view of the female twist lock member.

Now referring to FIGS. 11–15, the female twist lock member 50 is shown in greater detail. As shown in FIG. 11, the female twist lock member 50 has shoulders 52 and 54. The shoulders 52 and 54 extend radially inward into the hollow body of the female member 50. As also shown in FIG. 11, the shoulder 54 extends a greater arcuate distance around the longitudinal axis of the female member 50 than the shoulder 52. For best results, I prefer to have shoulder 52 extend for an arc of about 80° and have shoulder 54 extend for an arc of 90° around the longitudinal axis of the female member 50. As shown in FIGS. 13–15, each of the shoulders 52 and 54 has an inclined edge 53.

The inclined edge 53 on each of the shoulders 52 and 54 cooperates with corresponding inclined edges 51 on the shoulders 37 and 39. When the male member 30 and the female member 50 are joined and then rotated, the shoulders 52 and 54 and the shoulders 37 and 39 follow their respective inclined edges 53 and 51 to pull the male member 30 further into the female member 50 and therefore holder 60. For best results, I prefer to have the male member 30 move about .016 inches further into the female member 50 when the two are rotated 90° relative to each other. This movement ensures that the tubing 32 and ferrule 36 will press against the port 33 of the guard column 40 with enough force to obtain a leak-free seal, as shown in FIG. 3.

Figure 17:
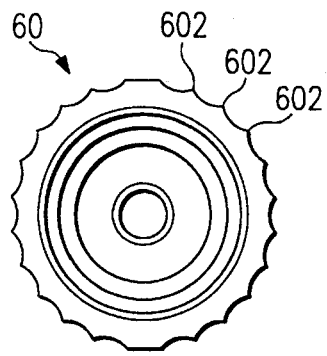
FIG. 17 is a frontal view of the holder.
Figure 16:
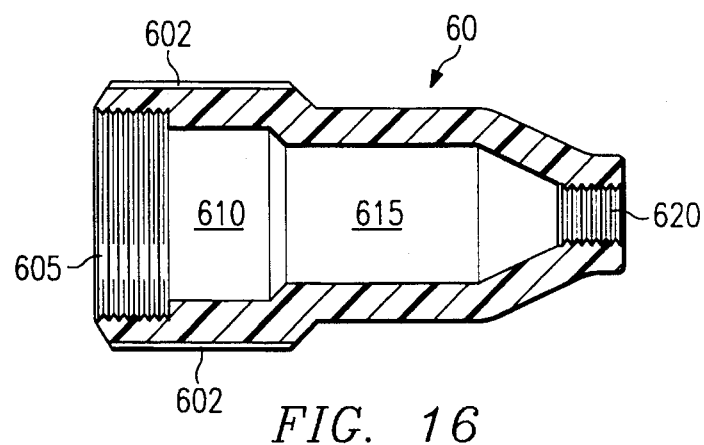
FIG. 16 is a cross-sectional view of a holder in accordance with the present invention.
Figure 18:
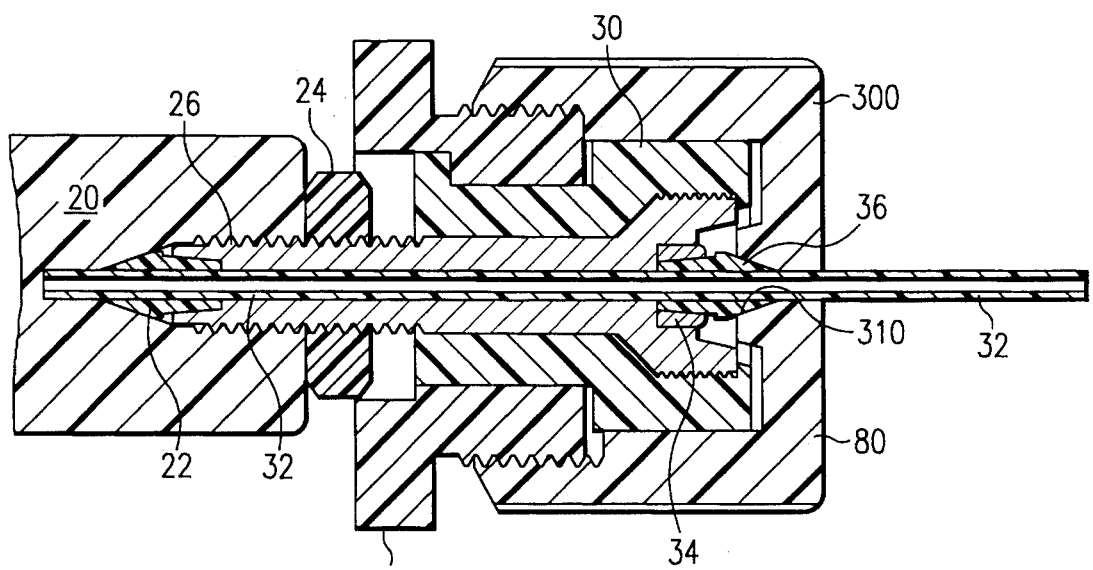
FIG. 18 is a cross-sectional view of a fixture used to cut tubing in the set up of the present invention.

Referring now to FIGS. 16 and 17, the holder 60 is shown in greater detail. As shown in FIG. 16, the holder 60 is generally hollow, with threaded counterbores 605 and 620 at its first and second ends, respectively. In addition, the holder 60 has a larger area 610 into which the female member 50 and male member 30 extend, and a smaller area 615 which is adapted to loosely hold the guard column 40 (as is shown in FIG. 3). In addition, the holder 60 has external ribs 602. The ribs 602 are located on the exterior of the holder 60 and run parallel to the longitudinal axis of the holder 60. The fibs 602 are provided to allow an operator to firmly grasp and rotate the holder 60 and therefore the female twist lock member 50, especially relative to the male member 30.

Preferably, the various components (except where otherwise noted) are made of the synthetic polymer polyetheretherketone, which is commercially available under the trademark "PEEK" from ICI Americas. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces.

ASSEMBLY AND OPERATION

Now referring back to FIG. 3, the complete assembly 100 is shown and its assembly and operation are described below. A conventional analytical or preparative column 20 includes a threaded counterbore (or a conventional end fitting with a threaded counterbore) at one end. The tube 32 is placed through the ferrule 22, the lock nut 24, the combination of the adapter 26 and the male member 30 (previously attached to one another), and a first end of the tubing 32 is placed against the bottom of the counterbore of the column 20. The adapter 26 and male member 30 are then removably secured to the column 20 by screwing the threaded portion 26a of the adapter 26 into the threaded counterbore of the column 20. Once adapter 26 has been screwed into the column 20, the metal lock nut 24 is tightened to ensure that the leak-proof connection between the column 20 and the tubing 32 remains secure and to prevent adapter 26 or column 20 from moving relative to each other. At this point, the tube 32 allows fluid communication between the column 20 and the unattached end of the tube 32.

Still referring to FIG. 3, a ring 34 and a ferrule 36 are placed over the second end of tube 32, which should initially extend beyond the end of the male member 30. Referring now to FIG. 17, a cutting fixture 300 is then placed over the tubing 32, ferrule 36, and ring 34. The cutting fixture 300 is attached to a female twist lock member 50. As shown in FIG. 17, a portion of the tubing 32 extends through a passageway in the cutting fixture 300. The cutting fixture is designed and adapted so that it matches the shape and dimensions of the guard column 40 which is to be connected to the column 20. Hence, the cutting fixture 300 has a port 310 which matches the size and shape of the port 33 of the guard column 40. Accordingly, an operator can remove the excess amount of the tubing 32 which extends beyond the passageway of the cutting fixture 300 by cutting it with a sharp knife or razor to thereby obtain a piece of tubing 32 of the correct length for connecting the guard column 40 to the primary column 20 with the assembly 100.

After the tubing 32 has been sized, the cutting fixture 300 is removed. One end of a guard column 40 is then placed over the second end of tubing 32, and the ring 34 and ferrule 36, as shown in FIG. 3. As noted above, the end fittings of the guard column 40 have tapered ports 33. The tapered ports 33 are adapted and designed to receive and hold the combination of the tube 32, the ring 34, and the ferrule 36 extending from the unattached end of the adapter 26.

Next, the combination of the holder 60 and the female twist lock member 50 (previously attached to each other) is attached. The female twist lock member 50 is secured to holder 60 by screwing it into the threaded counterbore of the holder 60. The open end of the female twist lock member 50 is placed over the unattached end of the guard column 40. The female twist lock member 50 is adapted and designed so that its shoulders 52 and 54 fit over and pass by shoulders 37 and 39 of the male twist lock member 30 when the male member 30 and the female member 50 are properly aligned. (It will be understood that in operation, the male member 30 can be inserted into the female member 50 or the female member 50 can be placed over the male member 30. Either way, the male member 30 and the female member 50 are easily joined by an operator.) The male member 30 and female members 50 are adapted and designed so that the shoulders 37 and 39 pass by shoulders 52 and 54. The holder 60 (and thus the female member 50 and shoulders 52 and 54) is then rotated relative to the male member 30, with shoulders 37 and 39 cooperating with shoulders 52 and 54 to hold member 30 securely within holder 60. As noted, the inclined edges 51 and 53 of the shoulders 37 and 39 and shoulders 52 and 54, respectively, cooperate to force the male member 30 further into the female member 50 (and therefore the holder 60 as well). At this point, the other end of the guard column 40 is securely attached to the LC system by way of tubing 70, ferrule 72, ring 74, and adjustment nut 65. The tubing 70 extends through the ferrule 72, the ring 74, and the nut 65, and is positioned in the port 33 of the guard column 40. The nut 65 can be screwed into the threaded counterbore 620 of the holder 60, thus forcing the ferrule 72 and tubing 70 into and against the port 33 of the guard column 40. The lock nut 62 is then tightened to secure the tubing 70 and nut 65 in place. Because the guard column 40 is attached at one end to the holder 60 and at the other end to the tubing 32, the movement by the holder 60 further towards the male member 30 also forces the guard column 40 against the tubing 32 and ferrule 36, thereby ensuring a leak-free connection of tubing 32 to one end of the guard column 40. By carefully controlling the size of the various components, fluid communication is allowed through leak-free connections between tubing 70 and through the guard column 40, through tube 32 and through the column 20.

To disconnect the guard column 40 from the column 20, an operator need only rotate the holder 60 relative to the primary column 20. Such rotation will thus rotate shoulders 52 and 54 relative to shoulders 37 and 39. After a rotation of about 90°, the shoulders 37 and 39 can be easily pulled between shoulders 52 and 54, thereby allowing quick and easy separation of the guard column 40 from the column 20. Once removed, the guard column 40 can be quickly replaced by another guard column 40' (not shown) of the same size.

At this point, an operator can simply place the new guard column 40' (not shown) on the ferrule 36 and tubing 32, place the holder 60 (to which the tubing 70 has remained attached and secured in place via nut 65 and lock nut 62) over the guard column 40' (not shown) and the male member 30, and then rotate the male member 30 and the holder 60 relative to each other, thereby forming leak-free seals between the new guard column 40' (not shown) and the primary column 20 and also the tubing 70.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiments and specific forms, materials, and the like are merely illustrative and do not limit the scope of the invention or the claims herein.

I claim the following:

1. An assembly for connecting a liquid chromatography column comprising:

a female member having a plurality of shoulders extending radially inward into its hollow body;

a hollow holder attached to said female member;

a guard column having first and second ends and positioned within said holder;

a male member having a plurality of shoulders extending radially outward from its body, wherein the shoulders of the female member and the shoulders of said male member cooperate to removably engage one another when said male member is inserted into said female member and said male member and said female member are rotated relative to each other thereby forming a twist lock, quick release mechanism; and means for connecting the first end of said guard column to a liquid chromatography system; and means for connecting the second end of said guard column to a primary column.

2. The assembly according to claim 1 wherein said means for connecting the first end of said guard column to a liquid chromatography system comprises:

a ferrule;

hollow tubing; and a male nut, wherein said nut is screwed into a threaded counterbore in said holder to press said ferrule and said tubing against the first end of said guard column.

3. The assembly according to claim 2 wherein said male member further comprises a lip adapted to stop said male member from rotating more than a desired amount relative to said female member.

4. The assembly according to claim 3 further comprising means for removably connecting tubing to a port of said primary column to said male member.

5. The assembly according to claim 4 wherein said means for removably connecting tubing comprises:

a hollow adapter firmly held within a longitudinal passageway through the body of said male member, wherein the tubing extends through said adapter and wherein one end of said adapter is screwed into a threaded counterbore in said primary column.

6. The assembly according to claim 1 wherein said female member has two shoulders and said male member has two shoulders.

7. The assembly according to claim 6 wherein each of the shoulders of said female member has an inclined edge and each of the shoulders of said male member has an inclined edge, with the inclined edges of the shoulders of said male member and said female member cooperating so that, when said male member is inserted into said female member and said male member and said female member are rotated relative to each other, said male member moves towards said guard column.

8. The assembly according to claim 1 wherein said male member, said female member, and said guard column comprise biocompatible materials.

9. The assembly according to claim 1 wherein said guard column has first and second ports which are conical.

10. The assembly according to claim 1 wherein said guard column has first and second ports which are flat-bottomed.

11. The assembly according to claim 1 wherein said male member has a lip adapted to restrict the rotation of said male member relative to said female member.

12. A biocompatible assembly for connecting a liquid chromatography column comprising:

a biocompatible female member having a plurality of shoulders extending radially inward into its hollow body;

a hollow holder having first and second ends, wherein the first end is attached to said female member;

a biocompatible guard column positioned within said holder;

a biocompatible male member having a plurality of shoulders extending radially outward from its body, wherein the shoulders of the female member and the shoulders of the male member are adapted to cooperate to removably engage one another and, when engaged, hold the male member and the female member together;

a biocompatible ferrule having a passage therethrough;

a biocompatible male nut having a passage therethrough;

biocompatible tubing positioned through the passage in said ferrule and the passage in said nut, wherein said nut is screwed into a threaded counterbore in the second end of said holder to press said ferrule and said tubing against the second end of said guard column; and means for removably connecting biocompatible tubing from a port of said primary column to the first end of said guard column.

13. The assembly according to claim 12 wherein each of the shoulders of said female member has an inclined edge and each of the shoulders of said male member has an inclined edge, with the inclined edges of the shoulders of said male member and said female member cooperating so that, when said male member is inserted into said female member and said male member and said female member are rotated relative to each other, said male member moves towards said guard column.

14. The assembly according to claim 13 wherein said female member has two shoulders and said male member has two shoulders.

15. The assembly according to claim 14 wherein the shoulders of said male member extend different arcuate distances around the body of said male member.

16. The assembly according to claim 14 wherein the shoulders of said female member extend different arcuate distances around the body of said female member.

* * * * *